United States Patent [19]
Mertens

[11] Patent Number: 5,104,323
[45] Date of Patent: Apr. 14, 1992

[54] METAL-CERAMIC FILLING FOR TEETH

[76] Inventor: Claus-Jürgen Mertens, Kösliner Strasse 14, D-7500 Karlsruhe, Fed. Rep. of Germany

[21] Appl. No.: 700,828

[22] Filed: May 16, 1991

[51] Int. Cl.$^5$ ............................................. A61C 5/04
[52] U.S. Cl. ................................... 433/226; 433/208; 433/218
[58] Field of Search ............... 433/226, 227, 208, 215, 433/218, 219, 180, 183

[56] References Cited
U.S. PATENT DOCUMENTS

| | | | |
|---|---|---|---|
| 375,167 | 12/1887 | Land | 433/226 |
| 4,431,418 | 2/1984 | Kienhofer | 433/183 |

FOREIGN PATENT DOCUMENTS

| | | | |
|---|---|---|---|
| 850649 | 9/1952 | Fed. Rep. of Germany | 433/226 |
| 2518355 | 11/1975 | Fed. Rep. of Germany . | |
| 3742134 | 6/1988 | Fed. Rep. of Germany . | |

Primary Examiner—John J. Wilson
Attorney, Agent, or Firm—Browdy and Neimark

[57] ABSTRACT

A metal-ceramic filling to be cemented into a cavity of a tooth (10), which consists of cast metal (1) on its side capable of bearing weight, on which a ceramic material (2) is applied by means of a firing technique. The cast metal (1) is thinner on its edge, so that it can be applied by rotation and finishing to a beveled area (12). The filling can be laterally extended into an occlusal cusp. The filling can be used as a bridge anchor.

20 Claims, 7 Drawing Sheets

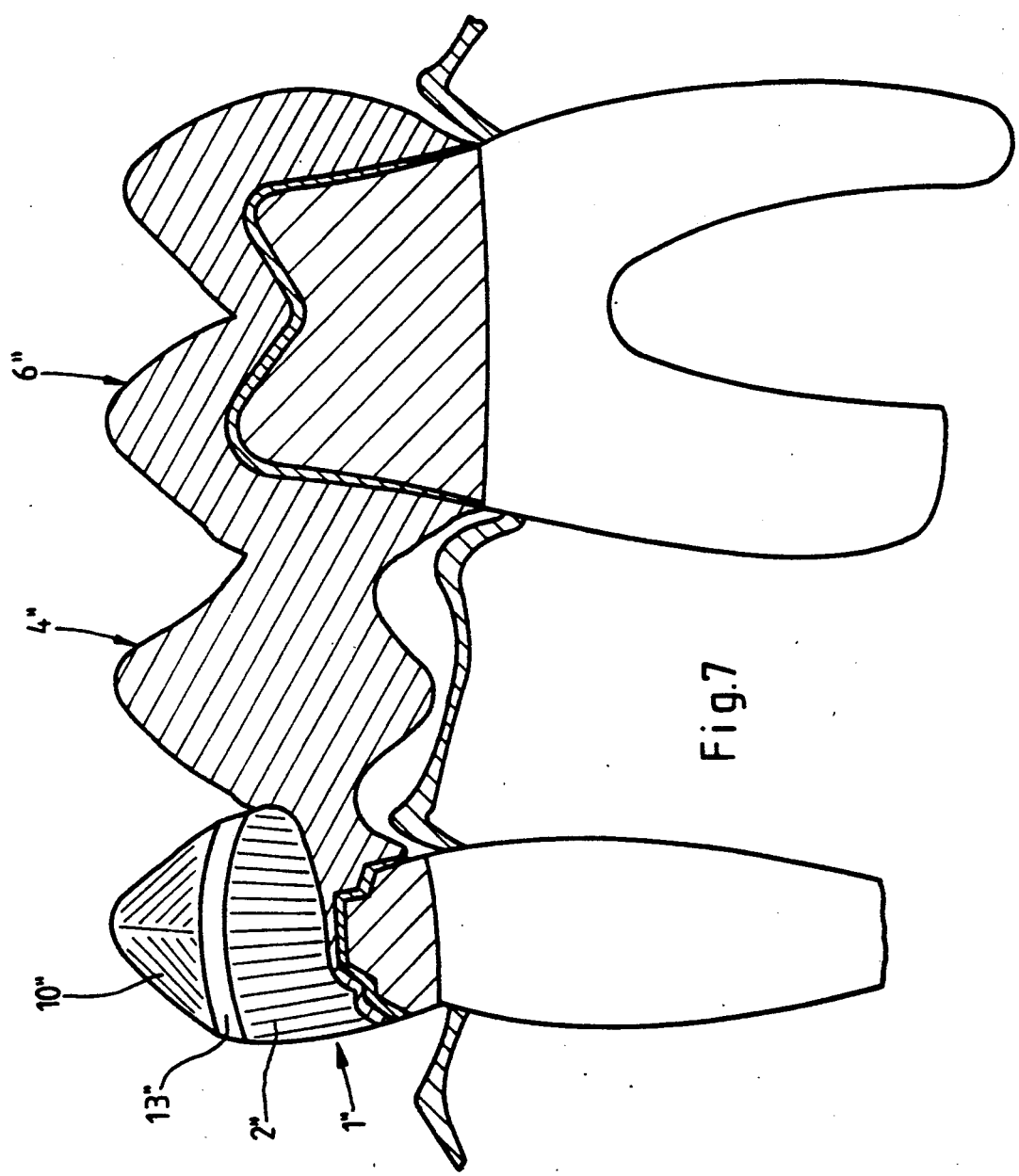

METAL-CERAMIC FILLING FOR TEETH

BACKGROUND OF THE INVENTION

1. Field of the Invention

The invention relates to a metal-ceramic filling for teeth to be cemented into a tooth cavity, comprising a ceramic filling that has a metal layer on the bottom and sides.

2. Description of Related Art

Metal ceramic fillings of this kind are already known from German Patent Disclosure Document 25 18 355 A1. It teaches a process for producing tooth crowns and dental fillings, in which a metal layer can be electrolytically deposited on a tooth model, and porcelain layers can be burned onto it. These metal layers may be of gold or a gold alloy with numerous other ingredients. The rim of the gold form may protrude and is polished, to achieve a tight fit in the gum region. An improvement in the dimensional accuracy and the fit at the periphery is attained with this process, as is an improvement in securing of the dental prostheses by means of the cement. The electrolytically deposited metal layer is smooth and ductile, and so it has limited adhesive strength and low flexural strength, and therefore only relatively small fillings can be made in this way and installed permanently.

It is also known from German Patent Disclosure Document 37 42 134 A1 to produce dental crowns in such a way that a ceramic layer having a thickness of from 200 to 300 μm is fired on an electrolyte metal foundation. Once again, because of its inadequate strength, this metal layer is not suitable for fillings subject to major strain nor does it assure tooth retention over the long term.

It is further known from German Patent Disclosure Document 36 05 437 A1 to use cast metal with fired ceramic for dental prostheses; the cast metal is used only to produce the rims and for bridge parts subjected to mechanical strains.

Metal ceramic fillings, also known as metal ceramic inlays or on-lays are known from the brochure by Wieland Edelmetalle K.G. entitled "AURO, die echte Goldverblend-Krone [AURO: the genuine gold veneer crown] 1989, which are made by a ceramic firing technique. To this end, copies of the tooth stumps are made in the laboratory, and the duplicate stumps are provided with copper contact bars and coated with conductive paint. This duplicate stump is coated with a thin gold layer approximately 0.2 mm thick by electrolytic deposition. Its gold content is 99.0 to 99.1%. After this layer is finished with a gold bonder, the ceramic composition is fired on in layers. This process is known as the AGC or Auro-Galva-Crown technique.

It is also known for ceramic compositions to be fired in the laboratory on a nonmetal tooth stump, in order to make ceramic fillings, also known as ceramic inlays or on-lays, without a metal base.

Ceramic inlays/on-lays are also known which, after optical scanning of the prepared cavity in the patient's mouth and after computer evaluation, are milled out of a porcelain block by a robot. Since the occlusion is quite inaccurate in that case, it has to be corrected in the mouth. The very high investment cost for the equipment must be considered a further special disadvantage of this production technique.

Plastic inlays/on-lays are also known, which are prefabricated either directly by prefabrication and adaptation with pre-hardening in the patient's mouth and possible subsequent definitive hardening in the laboratory, but the direct polymerization in the patient's mouth can be very damaging to the patient's tooth pulp; such plastic inlays/on-lays are also made in an indirect process. In that case, the plastic is built up not in the patient's mouth but rather in the laboratory after a mold of the jaw has been made, on the tooth stump of the master model, and polymerized in the laboratory.

The pure ceramic and plastic inlays/on-lays are typically secured with glass ionomer cement, which is an aluminum silicate polyacrylic acid cement. Glass ionomer cements are preferred over phosphate cements, because they have lower solubility and greater adhesion. Since the edges of the fillings of these inlays/on-lays cannot be finished and sealed off, the cement must perform sealing between the tooth and the filling with respect to the environment of the mouth, and must additionally assure a maximum of adhesion, because as a result of contractions when the ceramic is fired or the plastic is polymerized and because of the relatively smooth internal surfaces, the forces of retention without this special glass ionomer cement are relatively weak. In plastic inlays/on-lays, there is also the possibility of curing the cement by light polymerization. Permanent sealing of the filling, however, cannot be achieved with any of the glass ionomer cements, because despite the relatively low solubility, over the years they loosen the body of the filling causing a lack of tightness between the tooth and the filling. Even if the fillings are firmly seated, a microscopic gap forms in some cases because of the relatively major retraction when these cements polymerize. The result is a recurrence of caries. Another disadvantage is that pulp damage can occur upon polymerization in situ.

In all the inlays/on-lays mentioned above, a parallel preparation of the tooth cavity walls is sought, in order to achieve a favorable distribution of chewing pressure on the ceramic or plastic filling and to achieve the maximum possible frictional force. Often, however, this is not possible without greatly weakening the tooth. Especially in the side regions of the tooth, where the chewing pressure is the highest, a filling with occlusal cusp protection, that is, an onlay, of pure ceramic or plastic is contraindicated because of the high risk of fracture of this material; recourse must therefore be made to a cosmetically unappealing metal cast filling with occlusal cusp protection (onlay), or to a metal ceramic crown, with the disadvantage of greater loss of tooth substance and possibly long-term periodontal damage.

In all the previously known inlays/on-lays, there is generally a high risk of fracture, because a stabilizing metal foundation is lacking. In the aforementioned AGC technique as well, there is no stable metal foundation, since the gold layer, with a thickness of 0.2 mm, is very thin, and is also very soft because of the gold content of 99.0–99.1%.

All ceramic fillings have the advantage that they are made of a material the color of teeth which are durable in color, biocompatible, and occlusion-stable, or in other words have high abrasion resistance, and are relatively plaque resistant. In addition, the temperature accumulation and temperature conductivity of the ceramic are largely equivalent to that of the natural tooth.

Although plastic inlays/on-lays are of material the color of teeth, they do not keep their color over the course of years. They also have less tissue compatibility and a lower abrasion resistance than ceramic or gold cast fillings, with cavities being particularly likely to occur in the side regions of the tooth, and less plaque resistance and a less favorable temperature accumulation and temperature conductivity than ceramic fillings.

Both ceramic and plastic fillings can be brought into direct contact with a metal alloy or with amalgam, because no galvanic voltage difference arises.

One advantage of the previously known metal ceramic fillings made by the Auro-Galva-Crown technique is as follows:

Once the ceramic composition has been fired onto the approximately 0.2 mm thick gold layer, a narrow gold rim, which is 0.2 mm thick and is soft because of the 99.0 to 99.1% gold content, remains, extending around the outside of the tooth; this can be pressed down. Since this gold rim is very thin and soft, it must remain out of occlusal contact. However, additional stability and masticatory pressure distribution is not provided by the thin, soft gold coating, but since additional sealing is assured by pressing down such rim, the gold rim makes it possible to dispense with the glass ionomer cement and instead to use a known fine-grained phosphate cement, for instance so-called Harvard cement, for fixation. Closing the gap with a rotating tool to bend the gold rim (burnishing) in a fully sealed and completely finished manner is not possible, however, because it is too soft.

Gold inlays/on-lays are also known as fillings, which are made by casting from a relatively soft gold alloy with approximately 85 to 90% gold. These gold fillings have high stability and edge and pressure resistance. They are chemically resistant and corrosion resistant, and can be sealed well by pressing down, burnishing and finishing the rims during the setting phase of the cement. In the ideal case, the finishing serves to press the still-soft cement all the way beneath the edges of the filling, and the gold rim rests directly on the tooth without any intervening layer of cement. In particular, the rim of the tooth cavity is broken when the cavity is prepared, producing a so-called spring rim on the filling, in order to compensate for metal contraction and to enable finishing and burnishing of the gold inlay rim.

When there is a narrow, thin filling rim that comes into occlusal contact and because of the use of relatively soft gold alloys and often merely because of the breakage of the rim of the cavity, it is possible that after a few years the filling loses its tightness from abrasion, which can cause fissure caries. For firmly seating the gold filling, a fine-grained phosphate cement suffices, e.g. the so-called Harvard cement, and there is no need to use the considerably more expensive glass ionomer cement, with its disadvantages of low pressure resistance, greater porosity, greater film thickness and greater dimensional change, which can cause fissures to form. The abrasion of the occlusal surface of the filling is less than that of plastic but higher than that of ceramic. In the highly polished state, a gold filling is also more tissue-compatible than plastic, but less tissue-compatible than ceramic. Moreover, because of the galvanic voltage difference it is not possible to place a gold filling in direct contact with another metal alloy or amalgam. Otherwise, pulp pain and a metal taste can occur.

Another advantage is that strict parallelism of the tooth cavity walls can be dispensed with, because of the great stability and edge and pressure resistance of the filling. The particular disadvantages are that the metal is cosmetically unsatisfactory and forms a major temperature accumulator and has high temperature conductivity, which can cause sensations of pain.

SUMMARY OF THE INVENTION

An object of the invention is thus to achieve a metal ceramic filling that has greater stability and edge and pressure resistance than the previously known fillings, that permits burnishing and finishing, and that has a rough, readily bonded cementing surface.

In one embodiment of the present invention this is attained by providing that the metal layer comprises cast metal capable of bearing weight, and the ceramic filling is applied to the cast metal in a firing technique, and the cast metal has a thin, burnishable and finishable peripheral zone that is approximately 1 mm wide and approximately 0.3 mm thick. The metal layer is burnishable, namely the gap is closed with a rotating tool bending the soft metal layer. The metal layer is finishable by fixing and finishing the metal to the tooth material.

In another embodiment of the present invention the metal-ceramic filling comprises gold and metal alloys of types that are harder than the metal alloys used in cast gold fillings and that are used exclusively for the ceramic buildup technique. The result is much greater stability than in ceramic fillings, plastic fillings and the previously known metal ceramic fillings, as well as much higher edge and pressure resistance than in either of these previously known types of fillings or in cast gold fillings, as the gold alloys of the latter are softer. Accordingly, smaller dimensions can be provided and less material is consumed than in previously known cosmetically acceptable fillings, which is useful especially because of the higher torsional rigidity with two-surface and multi-surface fillings, such as mesial-occlusal-distal inlays. This great strength and in particular the torsional rigidity are also advantageous because of the favorable material properties of the cast metal and the structural embodiment of the cast article, because its U-shape, in combination with the angled edges, produces a cap-like profile, which has a high section modulus in every direction, for a relatively slight material thickness.

Another object of the present invention is to achieve greater filling stability as it is unnecessary to prepare the tooth with strictly parallel surfaces and valuable tooth substance is retained.

A further object of the present invention is to attain a very firm joint due to the natural roughness of the casting by using phosphate cement, which is easy to work, relatively inexpensive, and has a fine grain available, which also has relatively high pressure resistance, low porosity, a low film thickness, and exhibits only slight retraction.

It is another object of the present invention to achieve a metal-ceramic filling with a peripheral rim cement gap region achieving a seal by means of burnishing and finishing; this seal is more durable than with a gold cast filling, because as a result of the ceramic overlay the thermal strains with respect to the tooth are less than with a pure metal filling. The advantages of ceramic fillings are also attained, namely the tooth color of the material, its color durability, its maximum tissue compatibility or in other words biocompatability, its resistance to thermal shock, its maximum abrasion resistance or in other words occlusal stability, its plaque resistance, its temperature accumulation and temperature conductivity, which all are approximately those of the natural tooth. Without creating a voltage difference, the filling can be brought into direct contact with a metal alloy filling or an amalgam filling. Commercially available ceramic compositions for firing can advantageously be used. Cast alloys for firing ceramics of various noble metal content or of non-noble metal are suitable as the metal base; alloys with high Vickers hardness and high tensile strength can advantageously be used.

It is yet another object of the present invention to provide a metal-ceramic filling with optimal compatibility which is achieved using the ceramic onlay in such a way that it is drawn over the metal where the tooth filling comes into contact with the gum. In one embodiment the metal rim is relatively thin, for instance having a thickness of 0.3 mm, toward the rim of the cavity which is approximately 2 mm wide, while toward the rim of the cavity the metal rim is beveled with decreasing thickness and has an approximately 1 mm width without a ceramic overlay, which advantageously provides very good distribution of masticatory force between the filling and the tooth, and avoids a peak load on the tooth cavity edge that could cause the tooth material to crumble or the tooth wall to fracture.

In another embodiment due to its high stability, the metal foundation can extend from the filling as far as high-strained side regions. A bridge body for a crown, or some other previously known bridge anchor that is placed on the other side of a tooth gap, can be placed between two such fillings. This offers entirely novel possibilities for the dental prosthesis.

In yet another embodiment the cast metal of the novel tooth filling can be integrally made with a bridge body, or it can be soldered to a bridge body before the ceramic is fired, or it can be soldered after the ceramic is fired, if the adjacent bridge body comprises a solid casting.

BRIEF DESCRIPTION OF THE DRAWINGS

FIG. 7 shows a mesio-distal, sagittal section of a metal ceramic filling and a solid casting crown with a solid casting bridge body placed between them.

DESCRIPTION OF THE PREFERRED EMBODIMENT

The various fillings are shown in the installed state, so their advantages become readily visible. The fillings and the fillings with the bridge body can be made in dental laboratories and are thus independent commercial products. For dimensionally correct production of a metal ceramic filling, a tooth cavity is prepared in the patient with a rim beveled to approximately 2 mm wide, without strict parallelism of the cavity walls. This beveling of the rim of the tooth cavity having a 2 mm width is provided for the sake of maximum possible sealing of the filling, for compensating for the contraction of the metal of the cast metal base, and or a good distribution of masticatory force from the tooth filling to the tooth. After that, a model of the jaw is made. From the model, the master model is prepared in the laboratory, and wax modeling for the metal base is performed on the tooth stumps. The wax covers the walls of the cavity model to a thickness of approximately 0.5 mm, for instance ranging from 0.2 to 0.7 mm The wax model then serves to cast the metal base in the form of a lost casting core.

Figure 1:
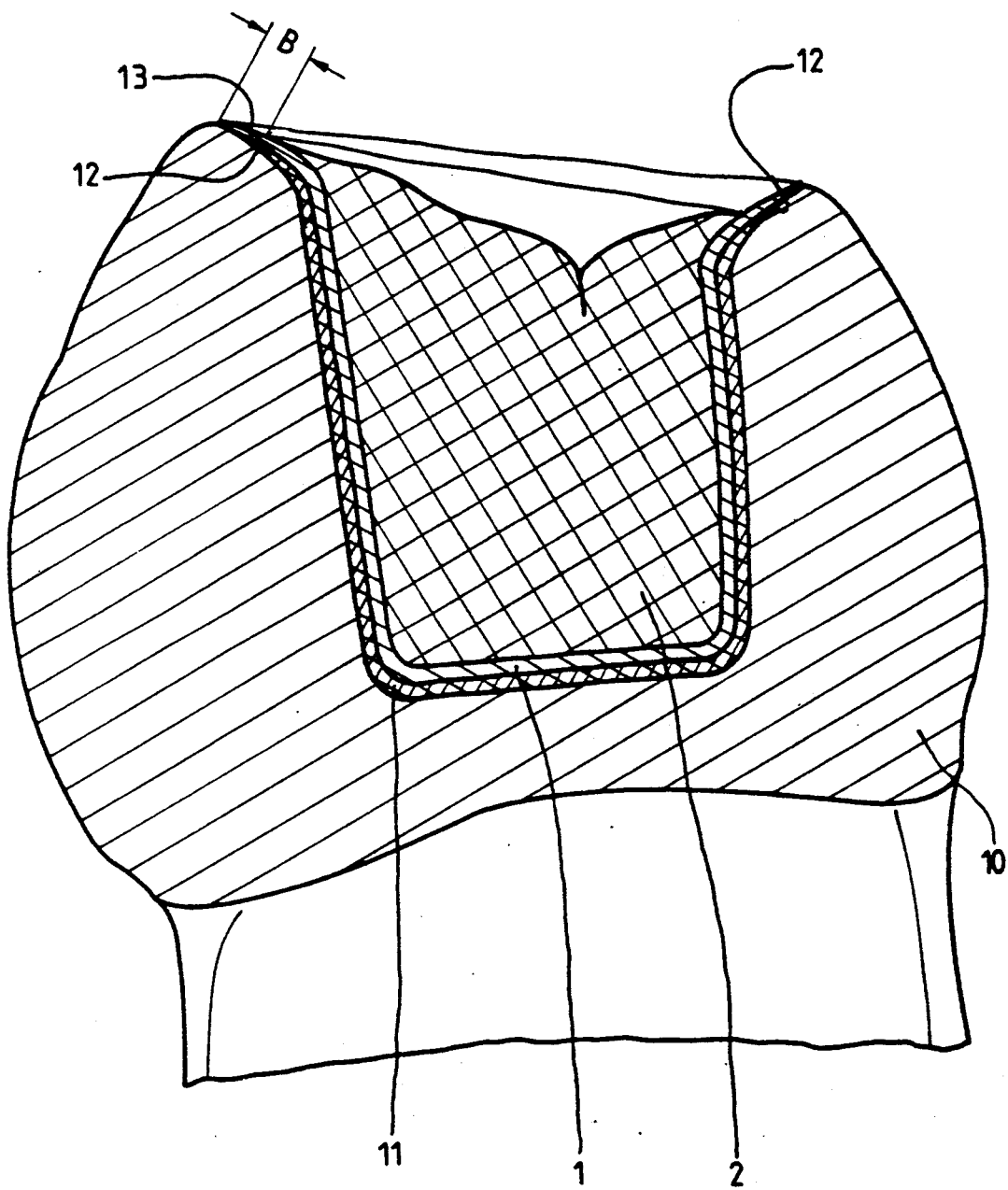
FIG. 1 shows a metal ceramic filling as an inlay in a tooth in a bucco-lingual section.

The metal base (1) can be seen in section in FIG. 1 It is inserted into the cavity of the tooth (10) at its wall and at the bottom, with a relatively thin cement layer (11), which extends approximately 1 mm wide underneath the approximately two millimeter wide beveled rim (12) of the base (1). The interior of the metal base (1) is filled with a ceramic composition (2) that is applied uniformly in layers and fired by a ceramic firing technique. The ceramic (2) bonds firmly to the oxide skin of the metal casting (1). No ceramic is applied to a peripheral zone (13) of approximately 1 mm width (B) of the beveled rim (12) Only where subgingival preparation in the approximal region is present is the metal covered completely with the ceramic composition as far as the rim, so that the metal rim does not come into contact with the gingiva. After the last firing, the exposed metal rim regions are reduced to a thickness of approximately 0.3 mm.

As the drawing shows, the width (B) of the peripheral zone (13) varies between approximately 0.5 and 1.5 mm, depending on the given characteristics of the cavity rim. The thickness of the peripheral zone (13) is likewise adapted to the given properties.

The exposed thin metal rims (13) are rotated and finished onto the tooth (10), as the drawing shows; this should advantageously be done when the cement (11) has not yet set, so that any excess of cement is expelled from the peripheral region and the metal rests flush with the tooth (10) on the periphery. The metal rim (13) extends outward in a tapered fashion because of this work and is extremely thin where it comes to an end.

Figure 2:
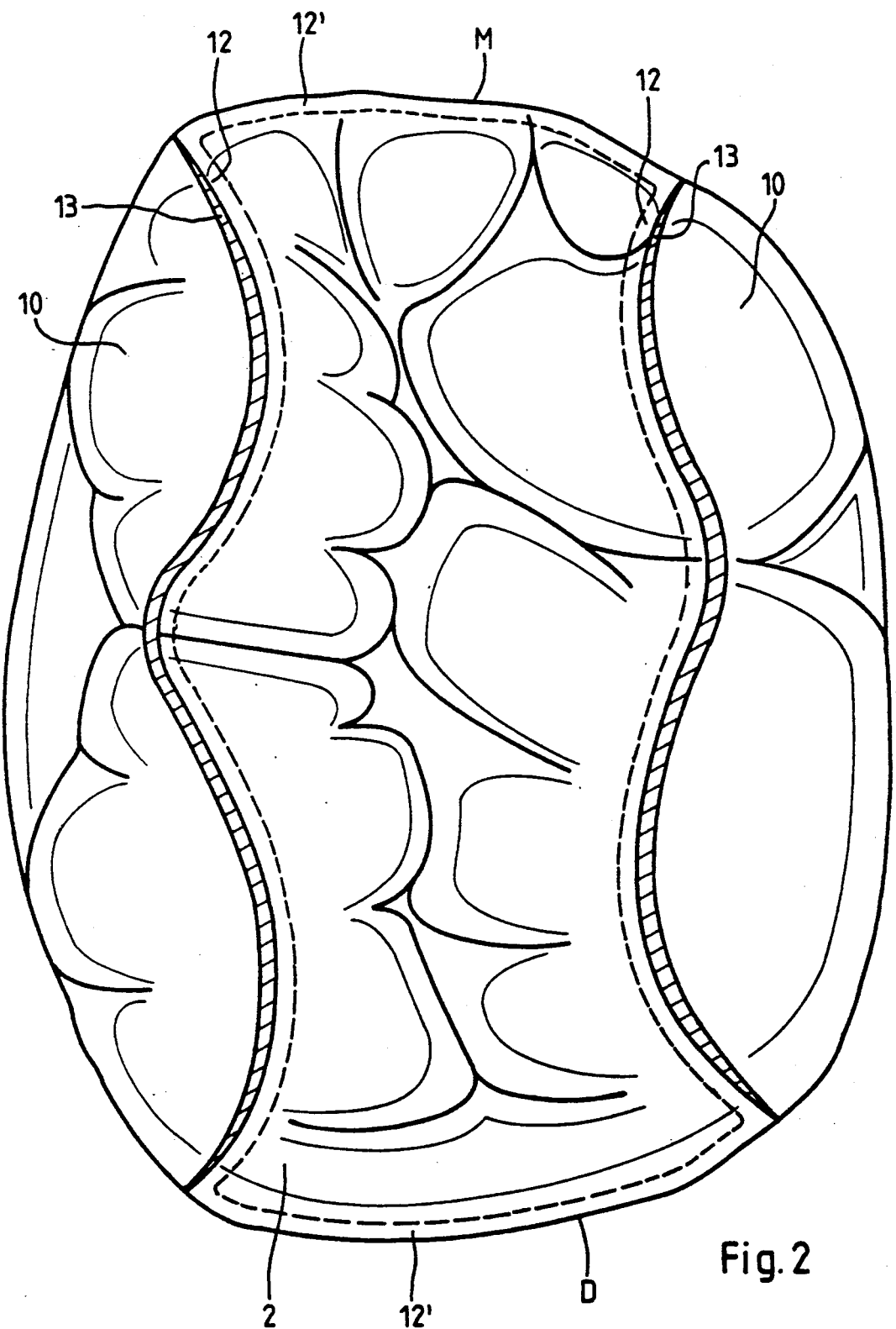
FIG. 2 is a plan view of the inlay of FIG. 1.

FIG. 2 is a plan view on a tooth (10) with a metal ceramic filling as an inlay. All that can be seen of the metal casting is the peripheral zone (13) of the beveled rim (12), the extent of which is represented by a dashed line. The middle region is filled with the ceramic composition (2). This composition is extended over the beveled portion (12') on the distal and mesial sides (D, M). On the top it is profiled in the manner of a tooth, as represented by the lines showing the height.

Figure 3:
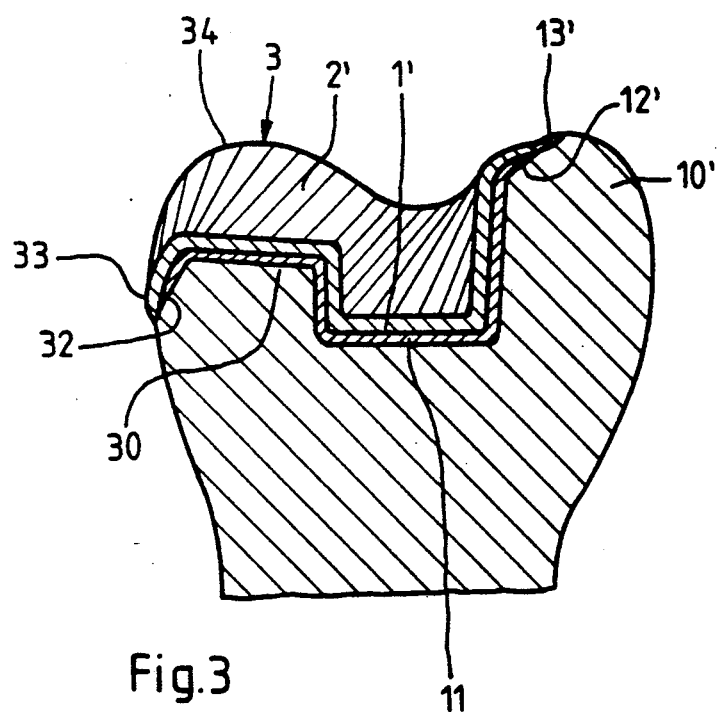
FIG. 3 shows a metal ceramic filling with an onlay on a tooth, in a bucco-lingual section.

FIG. 3 shows a section through a tooth (10') with an inserted metal ceramic filling that extends laterally toward the occlusal cusp (3). The metal casting (1') extends in a thickness of from 0.2 to 0.7 mm from the inner cavity across the lateral shoulder (30) as far as a beveled cavity rim (32). The ceramic (2') is fired thoroughly over this, and it forms an occlusal cusp (34) above the shoulder (30). The high-strength metal casting (1') provides load-bearing capacity and distribution of masticatory force. It has an exposed peripheral region (33, 13') on its circumference, which extends over the cavity rim (32, 12') and is burnished and finished there. The filling thus extends as far as the occlusal cusp and forms a structural part with it that is secured on and in the tooth (10') with the thin cement layer (11).

Figure 4:
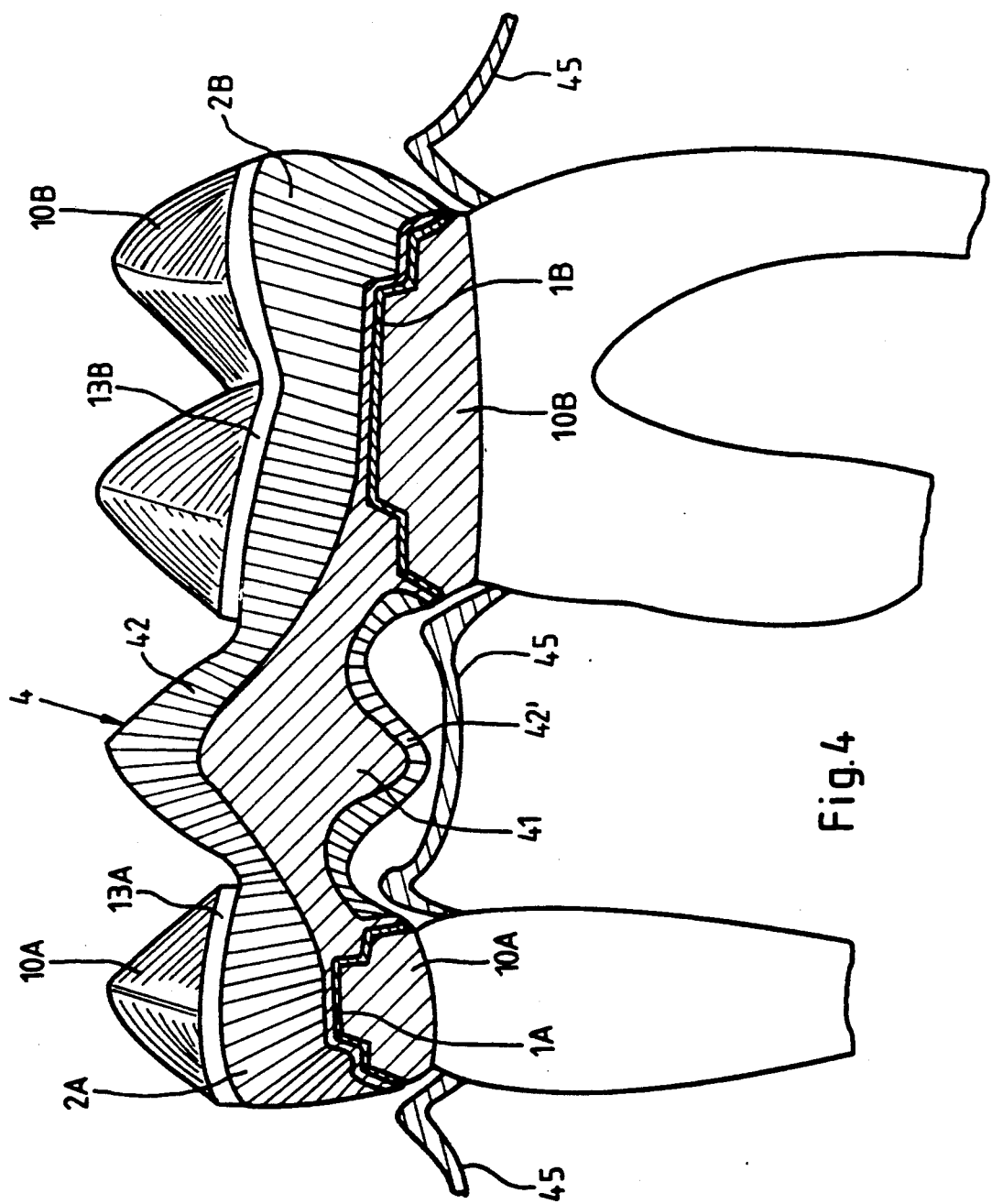
FIG. 4 shows a mesio-distal, sagittal section of two metal ceramic fillings of a bridge.

FIG. 4 shows a mesio-distal, sagittal section through two teeth (10A, 10B) with metal ceramic fillings and a bridge body (4) between them. The metal layers (1A, 1B) of the inlays are stepped as a supporting column toward the bridge body and from there extend, thickened toward the metal core (41) of the bridge body (4). The metal casting (1A, 1B, 41) is covered with the ceramic (2A, 2B, 42, 42'); the bridge body (4) is coated fully on the sides and bottom, and only the metal finishing rims (13a, 13b) are left exposed; they extend to the beveled portions of the teeth (10A, 10B). The ceramic covers the metal in the region of the gum (45).

Figure 5:
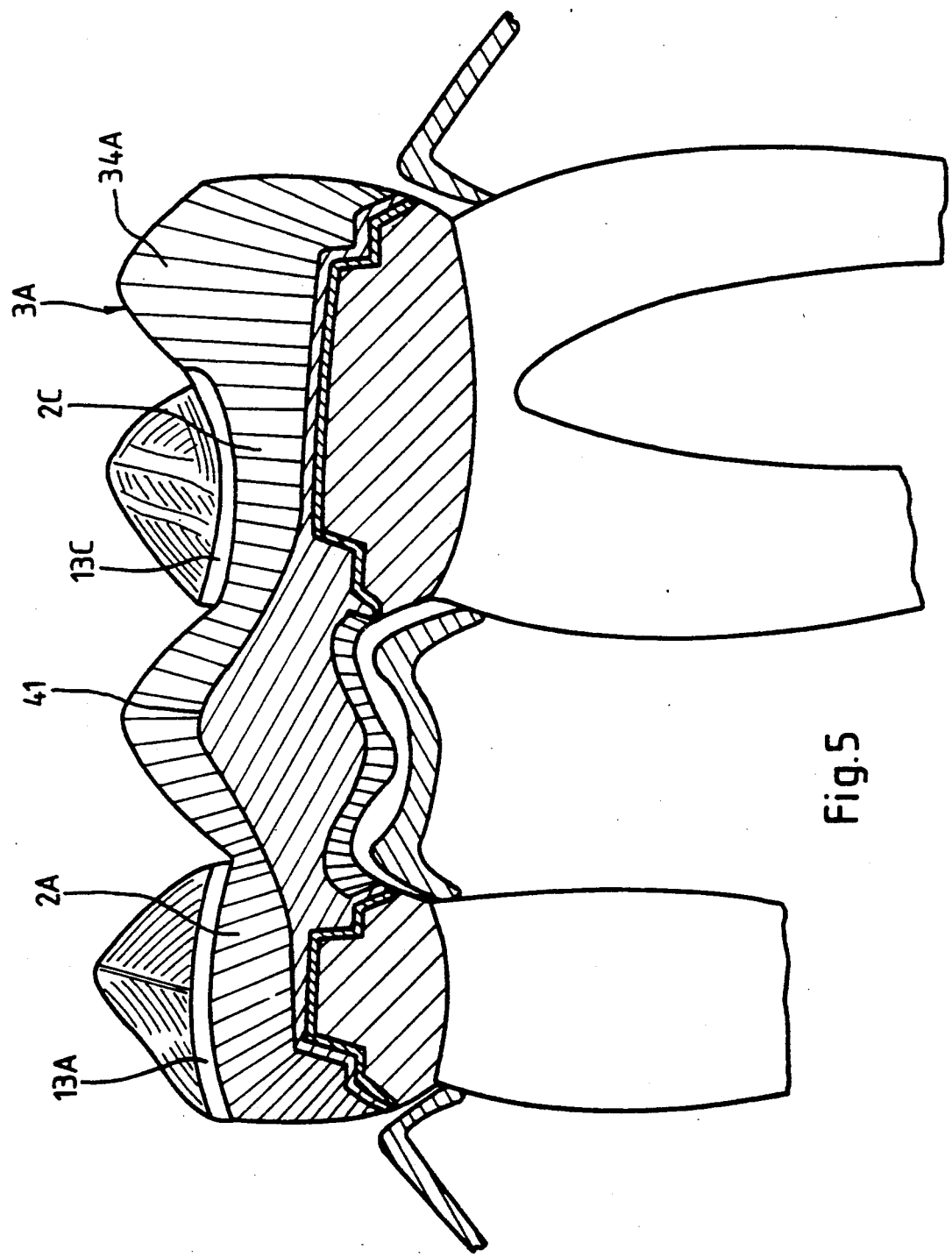
FIG. 5 shows a mesio-distal, sagittal section of two metal ceramic fillings of a bridge with an onlay.

FIG. 5 shows a bridge construction in sagittal section, with two metal ceramic fillings serving as bridge anchors; the ceramic extends from an ceramic inlay (2A) onward in the form of a bridge body ceramic onlay (41) to a further ceramic filling (2C), which forms an occlusal cusp (34A). The metal finishing rims (13A, 13C) provide sealing from the exposed tooth material.

Figure 6:
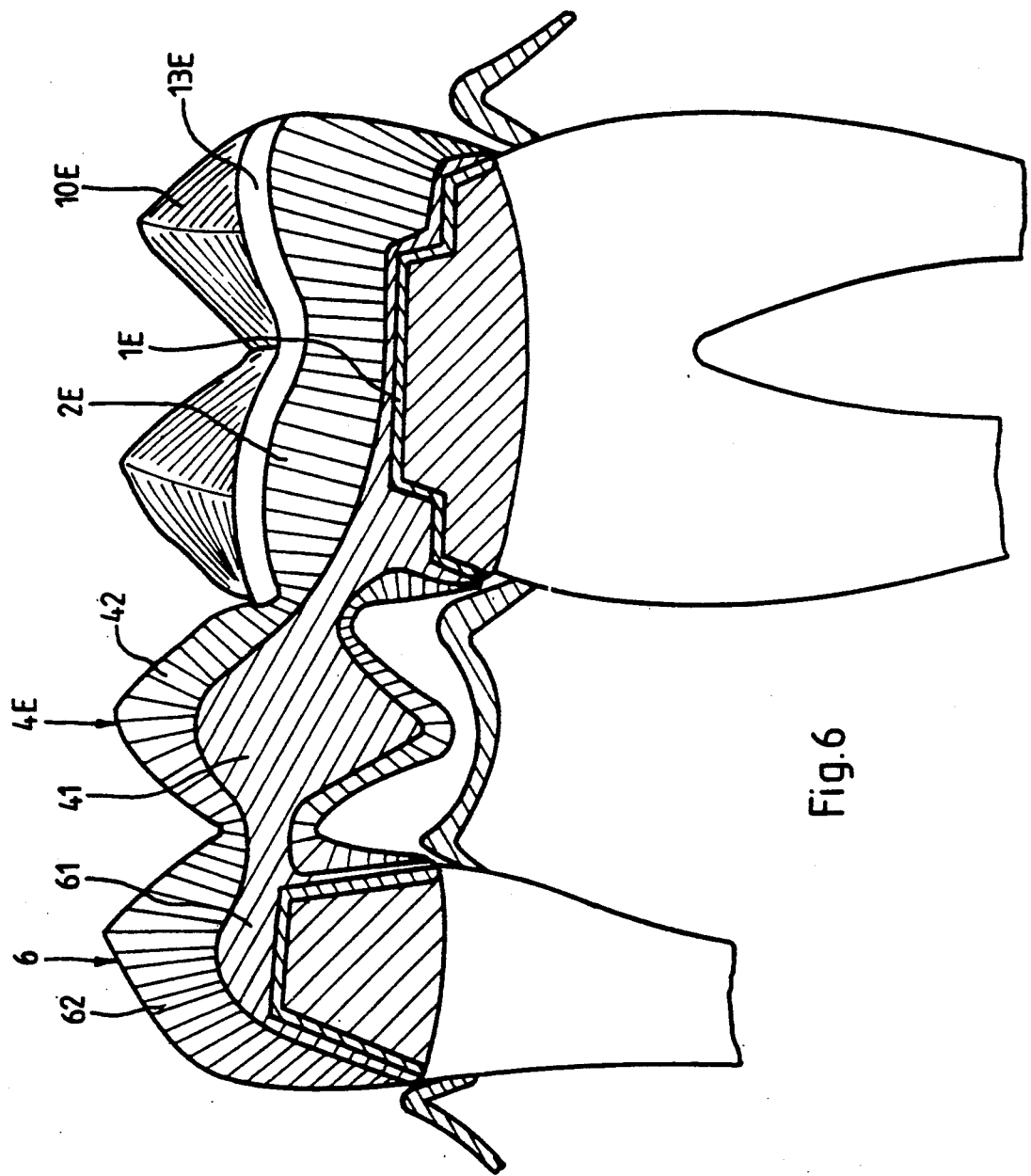
FIG. 6 shows a mesio-distal, sagittal section of a metal ceramic filling and a metal ceramic crown with a bridge body between them.

FIG. 6 shows a further combination of a metal ceramic filling, which is embodied as an inlay, with a bridge body (4E); on the other side, the bridge body has a metal ceramic crown (6) as a bridge anchor. The metal base (61) of the crown (6), the metal core (41) of the bridge body (4E), and the metal base (1E) of the inlay are made in one piece or are soldered together. Moreover, and around the bridge body region, the ceramic composition (62, 42, 2E) of the crown (6), bridge body (4E) and inlay (2E) are made cohesive. Only the finishing rim (13E) is exposed toward the tooth (10E).

FIG. 7 shows another bridge, one bridge anchor of which is a metal ceramic filling (1", 2"). The second bridge anchor is a solid cast crown (6"), and the bridge body (4") is also a solid casting. The two solid cast parts (4", 6") can be economically made in a known manner and soldered to the filling (1") after the ceramic (2") is fired. The ceramic onlay (2") thus does not extend to the bridge body (4") and the crown (6"). The ceramic (2") is preferably provided only in the highly visible region of a front tooth (10"), where the merely narrow visible metal rim (13") is more acceptable than if it were of solid metal.

The bridge body is shown with a solid core; latticework or hollow cores can also be used.

Some examples of materials which can be used in the metal-ceramic fillings are as follows:

EXAMPLE 1

Noble metal alloys having a white to pale yellow color, approximately 70–80% gold 15–20% platinum and palladium, 0.5% silver. Vickers hardness: 200–270; tensile strength: 530–740 N/mm².

EXAMPLE 2

Noble metal alloys having a golden color, more than 80% gold, the remainder platinum and palladium with a ratio of platinum to palladium greater than 1. Vickers hardness: 175–220; tensile strength: 520–620 N/mm².

EXAMPLE 3

Firing alloys with reduced noble metal, having 40–55% gold, 15–20% silver, and 25–35% palladium. Vickers hardness: 225–280; tensile strength 710–750 N/mm².

EXAMPLE 4

Nearly silver-free palladium/gold alloys with over 50% gold and approximately 40% palladium.

Other materials which can be used in the metal-ceramic fillings are:

firing alloys based on palladium and silver; firing alloys based on palladium; and firing alloys based on non-noble metal.

It is correspondingly possible for one skilled in the art to make other combinations of the metal ceramic filling with other components in dental technology; the connection in each case is made with the load-bearing metal body, and the ceramic can be applied continuously on it as an overlay.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A metal-ceramic filling for a tooth to be cemented into a tooth cavity and having at least one edge formed to terminate along an occlusal surface of the tooth upon placement into the tooth cavity, comprising
   a ceramic filling (2, 2', 2A, 2B, 2C, 2E) that has a metal layer (1, 1', 1A, 1B, 1E) of greater than 0.3 mm thickness on the bottom and sides, wherein said metal layer (1, 1', 1A, 1B, 1E) comprises cast metal capable of bearing weight, and said ceramic filling (2, 2', 2A, 2B, 2C, 2E) is applied to said cast metal in a firing technique, and said cast metal has a thin burnishable and finishable peripheral zone (13, 13', 13A, 13B, 13C, 13E) extending beyond said ceramic filling that is at least approximately 0.5 mm wide and approximately 0.3 mm thick.

2. A metal-ceramic filling in accordance with claim 1, wherein a peripheral zone (13, 13', 13A, 13B, 13C, 13E) is located in a beveled area (12, 12'), which is approximately 2 mm wide.

3. A metal-ceramic filling in accordance with claim 1, wherein said ceramic filling (2, 2', 2A, 2B, 2C, 2E) completely covers the rim of said cast metal (1, 1', 1A, 1B, 1E) in an area oriented towards the gums.

4. A metal-ceramic filling in accordance with claim 1, wherein said cast metal (1, 1', 1A, 1B, 1E) has a thickness of approximately 0.4 mm on the bottom and sides.

5. A metal-ceramic filling in accordance with claim 1 which includes an onlay (3) having an occlusal cusp (34), wherein said cast metal (1), extends below said occlusal cusp (34) on the side of the filling and the ceramic filling (2') extends over the cast metal (1') and forms the occlusal cusp (34).

6. A metal-ceramic filling in accordance with claim 5, wherein said case metal (1') extends from the edge of said only (3) ending in a thin peripheral region (33) which can be rotated and finished.

7. A metal-ceramic filling in accordance with claim 1, further comprising a bridge and a metal core (41) of a bridge body (4) integral with the cast metal (1A, 1B, 1E), and wherein said metal-ceramic filling extends from a first side and forms a bridge anchor of said bridge.

8. A metal-ceramic filling in accordance with claim 7 wherein said bridge body is surrounded by a ceramic material, which is fired on together with the ceramic material (2A, 2B) of the filling.

9. A metal-ceramic filling in accordance with claim 7, wherein on a side of the bridge body (4) opposite said first side a further metal-ceramic filling (2B) is formed as a bridge anchor.

10. A metal-ceramic filling in accordance with claim 7, wherein on a side of the bridge body (4) opposite said first side a crown (6, 6") is formed as a bridge anchor.

11. A metal-ceramic filling in accordance with claim 10, wherein said crown is a metal-ceramic crown (6).

12. A metal-ceramic filling in accordance with claim 10, wherein said crown is a solid cast crown (6").

13. A metal-ceramic filling in according with claim 7, wherein the bridge body (41) extends with an occlusal cusp (34) into the metal-ceramic filling, forming an onlay.

14. A metal-ceramic filling in accordance with claim 13, wherein the metal alloy is a material selected from the group consisting of:
  noble metal alloys having a white to pale yellow color, approximately 70–80% gold, 15–20% platinum and palladium, and approximately 0.5% silver and having a Vickers hardness of 200–270 and tensile strength of 530–740 N/mm$^2$;
  noble metal alloys having a golden color, more than 80% gold, the remainder platinum and palladium wherein the ratio of platinum to palladium is greater than 1, and having a Vickers hardness of 175–220 and tensile strength of 520–620 N/mm$^2$;
  firing alloys with reduced noble metal, having 40–55% gold, 15–20% silver, and 25–35% palladium and having a Vickers hardness of 225–280 and tensile strength 710–750 N/mm$^2$;
  nearly silver-free palladium/gold alloys with over 50% gold and approximately 40% palladium;
  firing alloys based on palladium and silver;
  firing alloys based on palladium; and
  firing alloys based on non-noble metals.

15. A metal-ceramic filling in accordance with claim 7, wherein said bridge body is made in one piece with said cast metal.

16. A metal-ceramic filling in accordance with claim 7, wherein said bridge body is soldered to said cast metal.

17. A metal-ceramic filling in accordance with claim 1, wherein the cast metal consists of a firing alloy on a noble metal base or a non-noble metal base and has a Vickers hardness between 150 and 300 and a tensile strength between 400 and 800 n/mm$^2$.

18. A metal-ceramic filling according to claim 1, wherein said cast metal layer has a substantially uniform thickness on said bottom and sides.

19. A metal-ceramic filling for a tooth to be cemented into a tooth cavity and having at least one edge formed to terminate along an occlusal surface of the tooth upon placement into the tooth cavity, comprising
  a thin cast metal layer having a generally cup-shaped configuration with an exterior surface adapted to fit tightly within the tooth cavity, said thin cast metal layer having a thickness of 0.2 mm to 0.7 mm, a tensile strength between 400 and 800 N/mm$^2$ and a hardness in the Vickers hardness range of 150–300 to provide high stability and high torsional rigidity, and
  a ceramic filling within said cup-shaped cast metal layer and adjacent an inner surface thereof, said ceramic filling being applied to said cast metal layer in a firing technique,
  said thin cast metal layer having at least one tapered edge extending beyond said ceramic filling, said tapered edge having a width of approximately 1–2 mm and a thickness of approximately 0.3 mm.

20. A metal-ceramic filling for a tooth cemented within a tooth cavity and having at least one edge terminating along an occlusal surface of the tooth, comprising
  a thin cast metal layer having a generally cup-shaped configuration with an exterior surface fitting tightly within the tooth cavity, said thin cast metal layer having a thickness of 0.2 mm to 0.7 mm, a tensile strength between 400 and 800 N/mm$^2$ and a hardness in the Vickers hardness range of 150–300 to provide high stability and high torsional rigidity, and
  a ceramic filling within said cup-shaped cast metal layer and adjacent an inner surface thereof, said ceramic filling being applied to said inner surface of said cast metal layer in a firing technique,
  said thin cast metal layer having at least one tapered edge extending beyond said ceramic filling, said tapered edge having a width of approximately 1–2 mm and a thickness of approximately 0.3 mm, said tapered edge being located in a beveled area approximately 2 mm wide.

* * * * *